US007723395B2

(12) United States Patent
Ringeisen et al.

(10) Patent No.: US 7,723,395 B2
(45) Date of Patent: May 25, 2010

(54) COMPRESSED POROUS MATERIALS SUITABLE FOR IMPLANT

(75) Inventors: Timothy A. Ringeisen, Exton, PA (US); Amanda Turner, King of Prussia, PA (US); Joseph DeMeo, Newtown Square, PA (US); Patrick E. Hearn, Aston, PA (US); Robert L. McDade, Downingtown, PA (US)

(73) Assignee: Kensey Nash Corporation, Exton, PA (US)

( * ) Notice: Subject to any disclaimer, the term of this patent is extended or adjusted under 35 U.S.C. 154(b) by 935 days.

(21) Appl. No.: 10/836,740

(22) Filed: Apr. 29, 2004

(65) Prior Publication Data
US 2005/0246021 A1 Nov. 3, 2005

(51) Int. Cl.
*A61F 2/02* (2006.01)
(52) U.S. Cl. .................. 521/50; 521/52; 623/16.11; 623/17.11
(58) Field of Classification Search .............. 428/304.4; 521/50, 52; 623/17.11
See application file for complete search history.

(56) References Cited

U.S. PATENT DOCUMENTS

RE29,487 E   * 12/1977  Gardner, Jr. ............... 128/152
4,501,269 A    2/1985   Bagby
4,660,755 A   * 4/1987   Farling et al. ............... 228/178
4,955,899 A   * 9/1990   Della Corna et al. ....... 623/1.46
5,013,324 A   * 5/1991   Zolman et al. ............. 623/23.3
5,282,861 A    2/1994   Kaplan
5,306,303 A    4/1994   Lynch
5,571,181 A   * 11/1996  Li .......................... 623/23.75
5,702,449 A    12/1997  McKay
5,986,169 A    11/1999  Gjunter
6,039,762 A    3/2000   McKay
6,241,771 B1   6/2001   Gresser et al.
6,346,123 B1   2/2002   McKay
6,371,988 B1   4/2002   Pafford
6,419,945 B1   7/2002   Gresser et al.
6,503,279 B1   1/2003   Webb
6,548,002 B2   4/2003   Gresser
6,569,201 B2   5/2003   Moumene et al.
6,572,619 B2   6/2003   Santilli
6,613,091 B1   9/2003   Zdeblick et al.

FOREIGN PATENT DOCUMENTS

DE    221 358    * 4/1985

* cited by examiner

Primary Examiner—Irina S Zemel
(74) Attorney, Agent, or Firm—Jeffrey R. Ramberg

(57) ABSTRACT

A high strength porous polymeric material manufactured by a compression process is disclosed. The material results in a network of interconnected collapsed pores, which forces thin overlapping walls and passages to be created. The network provides permeable access for fluid migration throughout the material. The strength and/or permeability are advantageous for medical devices and implants.

26 Claims, 8 Drawing Sheets

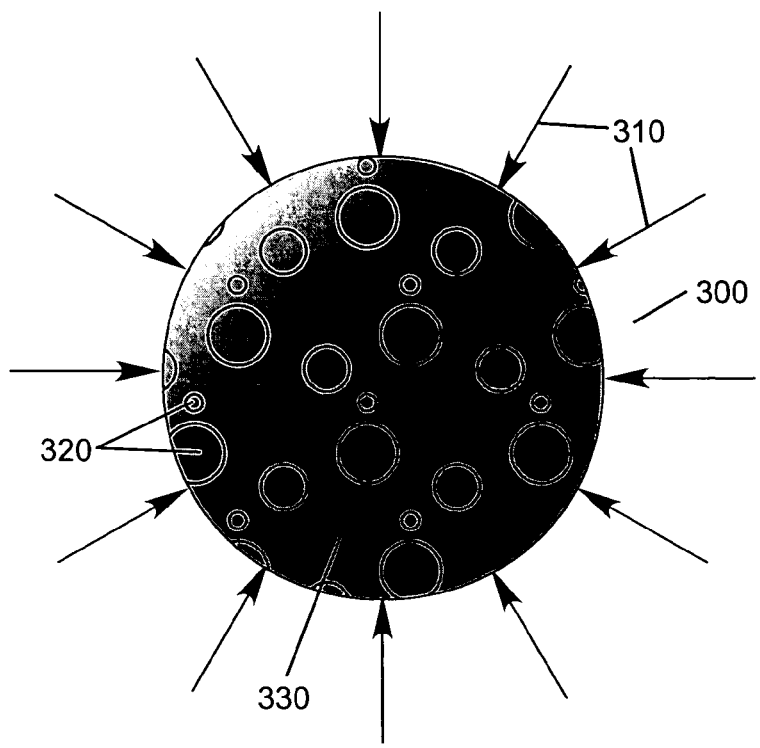
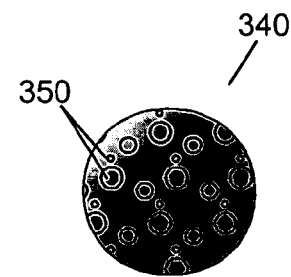
Fig. 3A
Fig. 3B
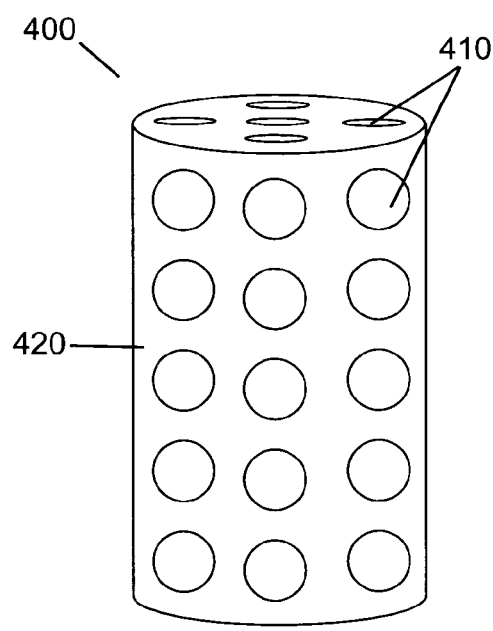
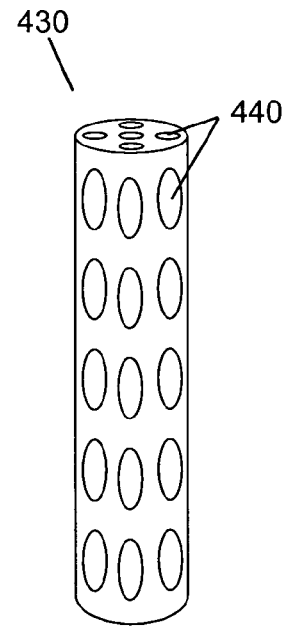
Fig. 4A
Fig. 4B

COMPRESSED POROUS MATERIALS SUITABLE FOR IMPLANT

BACKGROUND OF THE INVENTION

The present invention relates to surgical devices for stabilizing and/or fusing adjacent bone structures, and, more particularly, to surgical devices for stabilizing and/or fusing the spine and for implantation between the vertebrae, including the intradiscal space. Generally, this invention concerns internal fixation devices, particularly spinal fusion and related implants.

Spinal degenerative diseases (e.g., stenosis, disc disease, spondylosis, etc.) trauma, aging, or a herniated disc can cause compression in the spine thus applying pressure to the nerve roots and/or spinal cord. The compression produces progressive pain, loss of movement and sensation, and sometimes, permanent disability. Spinal fusion is among the standards of care for surgical decompression and stabilization of the spine. Fusion, known also as arthrodesis, is accomplished by the formation of an osseous bridge between adjacent motion segments. The goals of spinal surgery include relieving spinal cord/nerve compression, promoting spinal fusion, increasing stability, maintaining spinal alignment, and restoring disc height. Ideally, reconstructive surgery would result in total spinal fusion with an excellent clinical outcome.

For over 40 years, removal of the problematic disc and fusion of the adjacent vertebrae has been the common treatment for degenerative diseases. The classical surgical procedure is discectomy and interbody fusion with an iliac crest autograft with or without internal fixation. A discectomy typically requires the removal of a portion or the entire intervertebral disc. Different types of grafts (e.g., autograft, allograft, or synthetic ceramics) are used to fill the disc space.

Unfortunately, the use of bone grafts presents several disadvantages. Autogenous bone, which contains matrix molecules and living cells such as osteoblasts that facilitate fusion, is the ideal bone graft; however, postoperative pain is often greater at the harvest site than the surgical site. Additionally, autografts removed from a patient may not yield a sufficient quantity of graft material. Harvesting bone is also associated with high rates of harvest site morbidity and can increase the risk of infection and blood loss. Alternatively, allografts obviate the need for bone harvesting, but have inconsistent mechanical properties. Allografts can also transmit diseases or cause infections, and they have unpredictable and slow fusion rates. Autografts and allografts alone may not provide the stability required to withstand spinal loads and are subject to collapse or failure due to a lack of strength.

In the mid-1970's, Bagby found the clinical results of harvest site morbidity to be unacceptable. In U.S. Pat. No. 4,501,269, he describes the "Bone or Bagby Basket" to eliminate bone graft harvesting and promote bone fusion. Due to the drawbacks of traditional fusion techniques, his initial invention was important and innovative, and it has continually been improved in both design and material selection. These interbody fusion devices are designed to stabilize the vertebral bodies, hold osteogenic material, and promote early stabilization and fusion. The rigidity and structural design of the devices must be able to support the axial loads in the spine. Commercially available spinal interbody fusion devices are made of stainless steel, titanium alloy, carbon fiber, or allograft bone. Often, these devices have void spaces or perforations to allow bone ingrowth.

While carbon fiber and metal interbody fusion devices offer strength advantages, they have several disadvantages. Metal interbody fusion devices are a permanent foreign body and are difficult to remove during revision surgery. Due to the difference in mechanical properties of bone and metal, the main concern of metal interbody fusion devices is stress-shielding, which may cause bone resorption or osteopenia. Although these devices have demonstrated an ability to facilitate fusion, a sufficient fusion is not always achieved between the bone grafts housed within the cage and the vertebral endplates. Achieving a complete bony union in the middle portion of the cage has been particularly problematic. Clinical fusion outcomes may be difficult to assess with metallic interbody fusion devices due to the artifacts and scattering during postoperative CT or MRI scans. Often a complete bony union cannot be seen, making fusion results unreliable. Carbon fiber cages are radiolucent and have properties, such as modulus of elasticity, similar to bone; however, they are also a permanent foreign body. Long-term results with metal and carbon fiber interbody fusion devices are unknown due to the relatively recent development of the implants. Metal cages have been known to fatigue and will eventually fail if a solid bony fusion is not achieved. Over time, metal and carbon fiber cages may migrate or have significant subsidence into the vertebral bodies.

Gjunter (U.S. Pat. No. 5,986,169) describes a porous (i.e., 8 to 90% porosity) material made of a nickel-titanium alloy. The pores form a network of interconnected passageways that permit fluid migration through the material. The material may be used for biomedical implants or non-medical applications. Kaplan (U.S. Pat. No. 5,282,861) and Zdeblick et al. (U.S. Pat. No. 6,613,091) discuss a similar porous material made of a carbon-tantalum composite that could be used to create an implant device. The elasticity of the porous materials is similar to live bony tissue; however, most of the disadvantages associated with carbon fiber and solid metal internal fixation devices still apply to the porous nickel-titanium and carbon-tantalum alloy materials. For example, the porous metal implants remain permanently implanted in the body.

To avoid the disadvantages of metal and carbon fibers devices, bioresorbable materials have been used for years as sutures, bone plates, screws, pins, and other medical devices. A few advantages of bioresorbable implants include biocompatibility, predictable degradation, and complete resorption via natural pathways by the body over a period of time. Polymers are advantageous over other bioresorbable materials, such as ceramics, because they have high toughness and are highly reproducible. The toughness significantly reduces the danger of polymers failing by brittle fracture. Bioresorbable polymers can be formed into spacers, wedges, threaded cages, and a variety of other shapes (e.g., spinal interbody fusion devices).

Bioresorbable implants are transparent to x-rays, and therefore allow, for example, postoperative clinical assessment of a bony union, thereby overcoming one disadvantage of metallic implants. They can perform all the requirements of an interbody cage by providing immediate stability, maintaining foraminal distraction, restoring disc height, and allowing bone ingrowth and fusion. Bioresorbable interbody fusion devices can be produced that provide sufficient strength retention (up to 12 months or longer) in order to allow fusion to occur, then resorb after they are no longer needed. They have the compressive strength to withstand and carry the spinal axial loads; however, they have a modulus of elasticity similar to bone, which limits stress-shielding. Bioresorbable implant devices may feature or contain osteogenic material to attract bone and cells to the implant. Additionally, the bioresorbable devices may be hydrophilic and/or porous. Porous, hydrophilic devices promote the migration of fluid material into the implant, thus allowing a wide variety of tissue ingrowth. The porous bioresorbable implants are fully capable of being replaced by the patient's own bone growth.

Lynch (U.S. Pat. No. 5,306,303), McKay (U.S. Pat. No. 6,346,123) and Webb (U.S. Pat. No. 6,503,279) all describe bioresorbable, porous ceramic materials that may be used in medical implants. McKay and Webb specifically describe an intervertebral fusion device. Due to the brittle nature of ceramic materials, particularly as degradation occurs, the disclosed materials may not withstand the axial loads or cyclic loading of the implant site (e.g., spine) without fracture, collapse, and ultimately device failure.

McKay (U.S. Pat. Nos. 5,702,449 and 6,039,762) describes a spinal cage with an inner core of porous biocompatible material, preferably porous ceramic, which allows tissue ingrowth, and an outer body that can withstand compressive loads. The porous biocompatible material may protrude from the outer shell to permit contact with the vertebral bodies. The implant design with the resorbable inner core does not allow for the use of a bone graft within the device. A high strength outer shell may provide sufficient support; however, it brings concomitant property mismatch with natural bone. Bioceramics as used to form the outer shell are brittle and may fracture under high spinal loads.

Moumene and Serhan (U.S. Pat. No. 6,569,201) disclose a fusion cage with a structural bioresorbable layer disposed upon the outer surface of a non-resorbable support. The purpose of the non-resorbable support is to act as a scaffold for the bioresorbable layer and to hold a bone graft or osteogenic material. The bioresorbable layer would resorb over time, gradually increasing the loading on the bone graft and fusion cage. If the bioresorbable layer and bone graft degrade before fusion can occur, the non-resorbable support may cause stress-shielding. Depending on the thickness of the bioresorbable layer, complete degradation of the layer may cause a great decrease in disc space height. The non-resorbable support will remain a permanent foreign object in the body.

Gresser et al. (U.S. Pat. Nos. 6,241,771 and 6,419,945) describes a spinal interbody fusion device composed of 25-100% bioresorbable material. The device is composed of a resorbable polymer that can produce acidic products upon degradation and includes a neutralization compound to decrease the rate of pH change as the device degrades. In order to withstand the maximum physiologic loading, of at least 10,000 N (the maximum expected lumbar load), the disclosed device must be reinforced with fibers. The device is not porous, consequently limiting bone ingrowth. Similar to metal interbody fusion devices, the device may have void spaces to hold osteogenic materials, such as bone grafts or other osteogenic material. The disclosed device will slowly degrade and lose strength over time with complete resorption predicted to occur by one year. Clinically, complete fusion and bony union may take longer than one year in unstable patients. If fusion of the endplates through the disk space does not occur, the short-term resorption of the device may lead to collapse of the disk space.

Bioresorbable interbody spinal fusion devices offer solutions to disadvantanges related to bone grafts and metal and carbon fiber cages. Autografts require bone graft harvesting, which causes postoperative pain and morbidity at the harvest site. Allografts put the patient at risk for infection or transmitted diseases. Metal and carbon fiber cages remain permanent foreign bodies. Metal cages can cause stress-shielding and make fusion assessment difficult. They may also migrate from the implantation site or subside into the vertebral bodies. A need exists for an interbody spinal fusion device that achieves a successful fusion and bony union while avoiding drawbacks associated with the use of metal and carbon fiber devices or bone grafts.

SUMMARY OF THE INVENTION

The present invention is a compressed porous matrix material for application to a tissue site in order to promote new tissue growth. One aspect of this invention is glass transitional deformation or compression of a porous polymeric composition to create a high-strength material that retains the benefits imparted by its porous nature. The compression of the porous composition creates a three-dimensional multi-laminated structure having equivalent mechanical properties to solid (monolithic) polymeric structures without the problems associated with such structures. Compression can affect and create a new structure from the non-compressed porous matrix material. Certain compression methods may create collapsed pore walls that form thin, overlapping laminate walls. Because the laminate walls are formed from thin overlapping laminate walls wherein the walls form a continuous intercommunicating network within the device, the laminate layers are thereby limited in the amount that they can slide, thus eliminating this sliding or delaminating mode of failure, which may otherwise be seen. Depending on the amount of compression, the porous matrix material may have a few collapsed pores or may be completely made up of thin, collapsed pores. Variations in the compression method can create collapsed pores that did not form thin laminate walls, but instead the pores are condensed to a fraction of their original size. Due to pores that collapse or give way first, the pores throughout the material may vary in size. This compressed porous matrix material may be fabricated into many different devices for various applications in the body, which will be discussed later.

Any biocompatible polymeric material, which can to be fabricated into a porous matrix by those skilled in the art, is envisioned to be manufactured by the methods disclosed herein. Methods for creating a porous structure are well known to those skilled in the art (e.g., oil-water emulsions, lyophilization, precipitation, particulate leaching, critical gas blowing, gas forming polymerizations, etc.). As an example, one method involves dissolving a polymer in a solvent (e.g., acetone, chloroform, ethanol, dioxane, NMP, t-butanol, water, etc.) and filtering. The material is then treated to remove the residual solvent. Precipitating the polymer, evaporative distillation, lyophilizing the solution, or other methods may be used to remove the solvent, thus forming a porous polymeric material.

Another example involves dissolving a polymer in an organic solvent to prepare a polymer solution of high viscosity, or mixing a polymer solution in an organic solvent that does not dissolve the polymer to concentrate the solution as a gelatinous precipitate. A salt is homogeneously mixed with the polymer solution or gelatinous precipitate to give a polymer/salt/organic solvent mixed gel. The organic solvent is removed from the mixed gel through techniques known in the art (e.g., air dry, vacuum dry, sublimation, etc.) to produce an organic solvent-free polymer/salt composite. The composite is submerged in an aqueous solution or acidic solution to cause the salt to leach out at room temperature to form a porous three-dimensional polymeric structure. The porous three-dimensional polymer structure useful for the present invention may contain open celled intercommunicating pores and/or closed celled non-communicating pores.

The resultant porous matrix material is compressed by force; preferably, at temperatures at or above the materials glass transition temperature, but below the melt temperature. Any method of compression known by those skilled in the art is conceivable for this invention, including, but not limited to, using hydraulically or pneumatically powered platens or pistons to compress the porous matrix material. Other methods include using a screw or an arbor press to compress the material. Compression is defined as a method for applying force to a porous matrix material in order to alter the size, shape, mechanical/material properties, and/or structure of the original material. The compression has many variables, including the amount of force/pressure used, the percent compression of the original height, the direction of compression, etc. The percent compression directly corresponds to the amount of porosity after compression. It should be noted that although compression reduces the overall porosity of the material, surface area of the pores is minimally affected. The compression temperature can also be varied to create the desired properties of the material.

Those skilled in the art will recognize that polymers without a glass transition temperature can still be utilized in creating the above-described invention by means of inducing pseudo glass transitions. The simplest means of creating a pseudo glass transition is by incorporation of a plasticizer or plastisizing the polymer with small amounts of solvent. Other methods include, but are not limited to, quenching and cycling the temperature just above and below the melt point of the polymer. One skilled in the art will also recognize that these methods for creating pseudo-glass transition may also be effectively utilized for polymers having glass transition states.

Another aspect of this invention relates to controlled stretching and molding of a porous matrix material. Heating to temperatures above the glass transition temperature allow the porous polymer to soften and contract. If contraction is prevented and a force in a new direction is applied, the malleable polymer can be stretch to the extent that the porosity can collapse allowing the porous matrix to be pressed into or over a mold. Cooling at this time will lock in the new shape. The area of polymer that has been shaped is different than the unaltered areas. This is due to the forced alignment of the polymer partitions. Molds may be tailored to impart anisotropic effects at discrete locations throughout the implant, through creating areas of higher flow (i.e., more stretching) as well as areas of very low flow. Therefore, properties may be tailored by location and degree. Unlike the compressing method described above, this method has the ability to increase the surface areas within the porous matrix as the porosity is reduced.

Various medical uses of the above-described invention are described below. Other features or advantages of the present invention will be apparent from the following drawings and detailed description of the invention, as well as from the claims.

BRIEF DESCRIPTION OF THE FIGURES

FIGS. 3A and B illustrate the three-dimensional compression of a porous matrix sphere, including its pore structure before (3A) and after (3B) being compressed.

FIGS. 4A and B illustrates the three-dimensional compression of a porous matrix cylinder, including its pore structure before (4A) and after (4B) being compressed.

DETAILED DESCRIPTION OF PREFERRED EMBODIMENTS

Figure 1A:
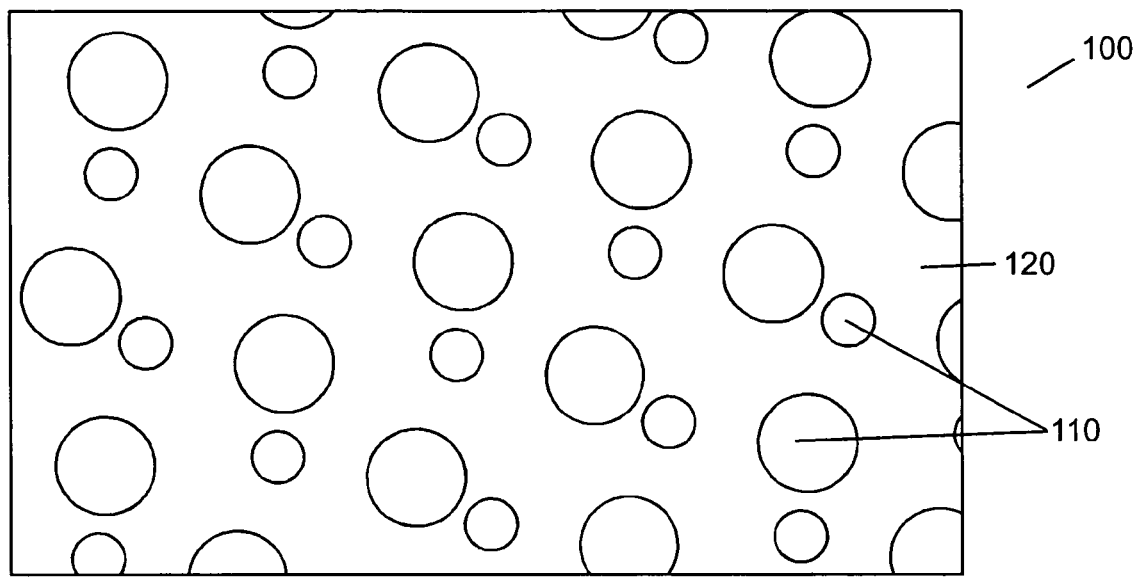
FIGS. 1A and B illustrate the porous matrix material, including is pore structure, before (1A) and after (1B) being compressed.

The object of the invention is an implantable prosthesis, constructed of a compressed porous polymeric material. The construction of the prosthesis is such that it is capable of absorbing energy and supporting large compressive loads utilizing less mass of material than would be necessary in the formation of a solid polymer prosthesis. Additionally, the device has advantages over metal prostheses, including the resorbable nature of the prosthesis and transient nature of its stress shielding.

While working to create a low porosity material, a new and unique method to control or alter the porosity within a porous material was discovered. In a preferred embodiment, the method for preparing the high-density porous matrix involves:
  a) creating a high porosity polymeric matrix by methods known in the art;
  b) inducing glass-transition within said porous polymeric matrix;
  c) applying a compressive force within one or more dimensions to achieve a new size or shape; and
  d) cooling the porous polymer out of the glass-transition wherein the polymer matrix maintains the new size or shape.

A method of producing a high density porous matrix that may experience glass transition after being compressed to a new size or shape involves:
  a) creating a high porosity polymeric matrix by methods known in the art;
  b) inducing glass-transition within said porous polymeric matrix;
  c) applying a compressive force within one or more dimensions to achieve a new size or shape;
  d) holding the porous polymer matrix above glass transition at the new size and shape for a period of time allowing the molecular chains within the matrix to rotate or move to a lower energy state; and e) cooling the porous polymer out of the glass-transition wherein the polymer matrix maintains the new size or shape.

Those skilled in the art will recognize porous materials that are not either brittle and/or susceptible to fracture (e.g. elastic polymers) do not need to be at glass transition prior to the compressive step, although, it may be required to place them in a state of glass transition while maintaining them in a compressive state to lock the material into the new conformation. Additionally, glass-transition may not be necessary for porous materials that do not naturally re-expand (e.g., porous metal) or that have been or will be contacted with a second substance that serves as a binder (e.g. bio-glue, adhesive, polymer solution) to lock the porous polymeric matrix in the compressed state. This binder can be an external coating or a substance that is flowed into the porosity and functions to hold the overlapping laminate walls together post compression. This binder may also be a temporary (e.g. biodegradable, dissolvable, heat sensitive) material that allows the compressed porous material to re-expand at a later time. This can be useful in filling voids that have small openings or for delivery of a compressed pellet through a cannula to a surgical site (e.g. spine) where it is allowed to re-expand and provide support. It would be obvious to one skilled in the art that a binder would not be necessary for a re-expanding foam if the compressed foam only re-expanded when placed in contact with body fluids or at body temp.

When the porous matrix material is compressed, some or all of the pores may be sacrificed and collapse to form laminate walls. The pores are limited in the amount they may move within the material structure before they must absorb the compression and/or torque. Some pores are sacrificed, giving way to other pores, which may stay structurally intact giving the matrix material an unique toughness not seen in prior art materials. Depending on the method, direction, and amount of compression, the sacrificed pores could give way in different modes (e.g., collapsing, folding, slipping, reducing in overall size, narrowing, etc.). The movement of some pores within the material and the sacrificing of other pores may cause the material to compress, thus changing the material and mechanical properties of the porous matrix material. The collapsing of the pores will have a direct effect on the porosity of the porous matrix material. The porosity will decrease during compression as pores are sacrificed and relieve compressive stress. The term "sacrificed" is used to both describes the initial collapse of pores during manufacture and any further changes to the pores in response to forces on the finished device. Toughness is partially imparted by the ability of a localized area within a device to independently accommodate stresses.

Compression can create a new structure within the porous matrix material. Certain compression methods may create collapsed pore walls that form thin, overlapping laminate walls. The laminate walls may be adjacent to each other, as in the case where compression has been applied to completely collapse the pores. Alternatively, the laminate walls may have some space or material between the walls, such that they are not in direct contact with each other (i.e., not adjacent). Because the laminate walls are formed from the collapsed pores, the layers are limited in the amount that they can slide, thus eliminating a delaminating or sliding mode of failure. Variations in the compression method and parameters can create collapsed pores that did not form thin laminate walls, but instead pores are condensed to a fraction of their original size. Because pores closest to the applied force typically collapse or give way first, the pores throughout the material may vary in size, creating an altered pore size distribution throughout the material. Given walls of equal thickness, larger pores are more likely to collapse than smaller pores. This can be used to reduce overall variation in pore size. Other methods for compression can produce tubular pores that are narrowed, lengthened, and/or collapsed. The tubular pores can span the length of the material or be interconnected. In all cases, compression parameters may be modified to produce material suitable for end use as a medical device.

The structure of the porous matrix material also depends on the amount of compressive force applied to the material. The amount of compression may change the porosity of the porous matrix material. The pore size distribution will also be affected by the amount of compression as the porous matrix material may be compressed so that only certain areas have collapsed pores, or so that all of the pores are sacrificed and collapse. The direction of compression in relationship to the original structure of the porous matrix material can also affect the structure of the compressed porous matrix material. For example, if the initial porous matrix material has long tubular columns, a force applied circumferentially to the material will collapse the diameter of the columns; whereas a force applied parallel to the axis of the columns will shorten the column length.

Compression of the porous matrix material can be controlled to create various structural patterns within the material; likewise, the mechanical properties of the material may be altered to meet specific requirements. The amount of compression is directly related to the maximum compressive load of the material. The more the material is compressed, the greater the maximum compressive load will be. If a medical device fabricated from the compressed material must withstand loading from more than one direction, the compressed material can be compressed three-dimensionally to increase the mechanical strength of the material in all directions. If the medical device is axially loaded, the compressed material may be compressed in one direction to optimize the mechanical properties of the material in that direction.

Generally, solid non-elastic, non-porous polymeric materials (i.e., polylactides, poly-dl-lactide, etc.) have good mechanical strength; however, they are brittle and will catastrophically fail under high compressive loads. Compressed porous material exhibits more ductility and toughness compared to the same non-porous polymeric material. The compressive porous material has the ability to absorb energy by sacrificing pores. As compression continues beyond the point when all the pores have collapsed, the material may expand slightly and microcracks will occur along its surface, thus avoiding catastrophic failure.

Preferably, porous polymeric materials (fibrous and/or non-fibrous) are compressed for the present invention, although it is also envisioned that porous metallic materials (fibrous and/or non-fibrous) may also be compressed. It should be noted that many of the benefits imparted to polymeric materials, including ductility and toughness would also be imparted to compressed porous metallic materials. Thus it is another object of the invention to create improved, lightweight porous metallic implants useful in orthopedic surgery (e.g., artificial hip implants, bone plates, femoral nails, screws, etc.).

The temperature of the porous matrix material (e.g., glass transition temperature) during compression can greatly affect the behavior of the final material. More specifically, the relationship between the compression temperature and the material's glass transition temperature plays a vital role in the properties of the final material. Glass-transition is defined as the state during which the molecules making up the matrix are free to move and rotate in an effort to achieve a lower energy state. At temperatures narrowly above the glass transition temperature, and below the melting temperature, the molecule alignment will occur more slowly than would alignment at temperatures further above glass transition, but still below melting temperature. Those skilled in the art will recognize that polymers with an extremely high glass transition temperature, or even no glass transition, can still be utilized in creation of the present invention by means of inducing pseudo glass transitions. The simplest means of creating a pseudo glass transition is by incorporation of a plasticizer or plasticizing the polymer with small amounts of solvent. This can be done by blending a plasticizer into the polymer or exposing the polymer to an atmosphere of molecules that would solvate the polymer at higher concentrations. Other methods include, but are not limited to, quenching and cycling the temperature just above and below the melt point of the polymer. Quenching allows crystalline polymers to become amorphous for a short period of time and may in turn create a pseudo glass transition below the melt point of the polymer. Cyclic heating and cooling of a polymer just above and below its melt point can be used to simulate a glass transition by retarding collapse of the porous structure. If the material is compressed below the glass transition temperature, stress can be locked into the material. If the material is then exposed to temperature at or above the glass transition temperature, the stress will be relieved and the porous matrix material may expand and possibly return to its pre-compression dimensions. Yet, if the material is compressed at a temperature at or above the glass transition temperature or brought up to glass transition after compression while still being compressed, the polymer chains in the material are free to rotate and assume a lower energy state. This may eliminate the stress in the compressed material and the material will retain its dimensions even when exposed to temperature at or above the polymer's glass transition temperature for a period of time.

If not compressed initially into the final shape, after being compressed and removed from the compression device, the porous matrix material may be machined into a new shape or design with various features. Machining processes for polymeric materials are well known to those skilled in the art. (e.g., coring, milling, sawing, lathing, etc.) As an example, a tubular device could be machined by coring out the inner diameter and then using a lathe to create the proper outer diameter.

The porous matrix material may be compression molded into an initial or final design of a medical device. If the device has complicated geometry, various features may be machined after compression molding, creating a refined shape for the device. As discussed above, the material and mechanical properties of the final device can be altered by the compression or mold temperature, the amount of overall compression, the design of the mold, etc. The porous matrix material may be compressed before molding or all the compression may occur during the molding process. The direction of compression before or during compression molding may also affect the mechanical properties of the device. For example, a cylinder of porous material may be three-dimensionally compressed and then compression molded into a threaded bone screw. Additionally, if the mold is heated and compression is performed rapidly, only those areas in direct contact with the mold will achieve glass transition, and collapse in response to compression. In this manner, a device having bi-modal pore structure can be created, as the pores in the center remain unaltered by compression.

The prosthesis may be sterilized by any method known in the art (e.g. exposure to ethylene oxide, hydrogen peroxide gas plasma, e-beam irradiation or gamma irradiation, etc.). The sterilization process minimizes the opportunity of infection to occur as a result of the implant.

In a preferred embodiment of the invention, a porous medical device is manufactured from a resorbable material, although this is not meant to exclude the use of non-resorbable polymers and metals. Different polymers, molecular weights, additives, processing methods, and sterilization methods can be used to control the resorption rates of resorbable polymers. Resorption rates can be adjusted to be shorter for applications that require mechanical strength for only a short period of time or longer for applications that require mechanical strength to be present for a longer duration. The materials of the construct may be fibrous or non-fibrous. Examples of resorbable polymers that can be used to form medical devices are shown in Table 1. These materials are only representative of the materials and combinations of materials that which can be used as implant materials.

TABLE 1

Examples of Bioresorbable Polymers for Construction of the Material of the Current Invention.

Alginate
Aliphatic polyesters
Cellulose
Chitin
Chitosan
Copolymers of glycolide
Copolymers of lactide
Elastin
Fibrin
Glycolide/l-lactide copolymers (PGA/PLLA)
Glycolide/trimethylene carbonate copolymers (PGA/TMC)
Glycosaminoglycans
Lactide/tetramethylglycolide copolymers
Lactide/trimethylene carbonate copolymers
Lactide/e-caprolactone copolymers
Lactide/s-valerolactone copolymers
L-lactide/dl-lactide copolymers
Methyl methacrylate-N-vinyl pyrrolidone copolymers
Modified proteins
Nylon-2
PHBA/g-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Collagen
    Types 1 to 20
        Native fibrous
        Soluble
        Reconstituted fibrous
        Recombinant derived
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)

TABLE 1-continued

Examples of Bioresorbable Polymers for Construction of the Material of the Current Invention.

Polypeptides
Polyphosphazenes
Polysaccharides
Polyurethanes (PU)
Polyvinyl alcohol (PVA)
Poly-b-hydroxypropionate (PHPA)
Poly-b-hydroxybutyrate (PBA)
Poly-s-valerolactone
Poly-b-alkanoic acids
Poly-b-malic acid (PMLA)
Poly-e-caprolactone (PCL)
Pseudo-Poly(Amino Acids)
Starch
Trimethylene carbonate (TMC)
Tyrosine based polymers For the purposes of promoting an understanding of the principles of this invention, reference will now be made to the embodiments illustrated in the drawings, where like numbers refer to like components, and specific language will be used to describe the embodiments and elements of the embodiments. It must be understood that no limitation of the scope or applications of the invention is thereby intended. For ease of understanding, pores are represented in the drawings by closed circles, it is recognized the pores may in fact be formed in various shapes, textures and interconnectivity (e.g., they may be interconnected or separate, open cell or closed cell, organized or random, and/or reticulated structures).

Figure 1B:
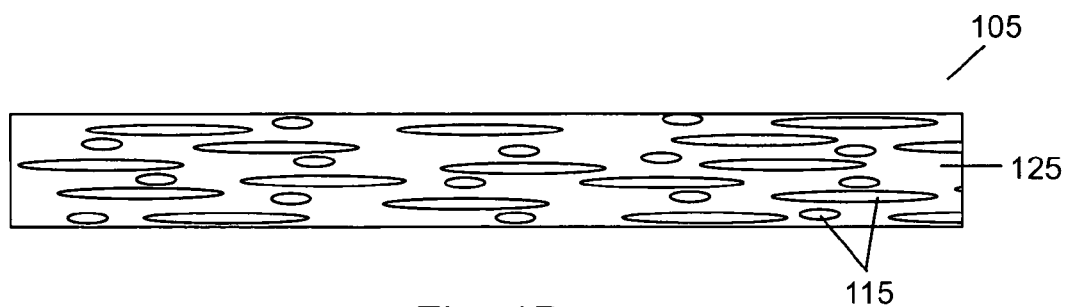

Referring now to the drawings, FIG. 1A depicts the porous matrix material 100 before any compressive force has been applied. The porous matrix material 100 includes a large percentage of void space, which is occupied by pores 110. The pores 110 form the structure within the polymeric material 120. After being compressed, as depicted in FIG. 1B, the compressed porous matrix material 105 contains the same amount of polymeric material 125; however, the sacrificed, collapsed pores 115 have reduced the porosity of the material.

Figure 2A:
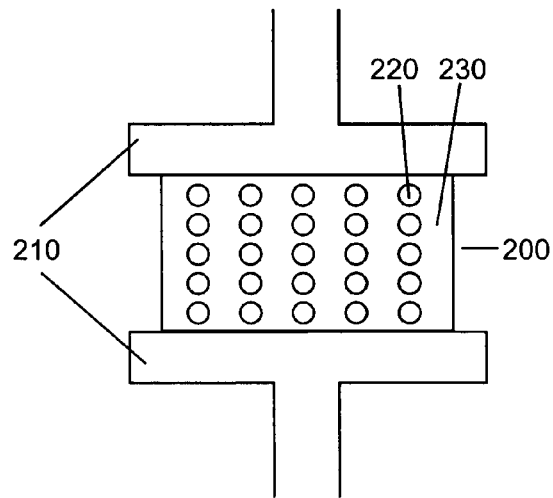
FIG. 2A illustrates the porous matrix material between two compressive devices.

In another embodiment, as depicted in FIG. 2A, uncompressed porous matrix material 200 is placed between two devices capable of applying compressive force 210 (e.g., platens, pistons, etc.), which may or may not be heated. The pores 220 and polymer material 230 define the structure of the uncompressed porous matrix material.

Figure 2B:
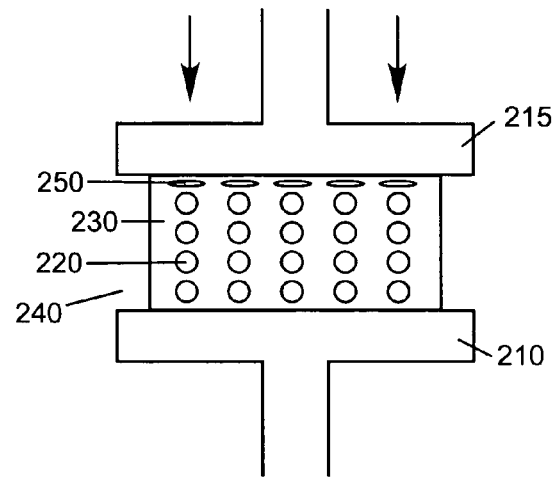
FIG. 2B shows the porous matrix material being compressed by the top compressive device.

As depicted in FIG. 2B, the compressive device 215 is actuated to create partially compressed porous matrix material 240. Upon compression of the material 240, a gradient is formed, wherein the compressed pores 250 first begin to collapse, while the pores 220 (depicted here in FIG. 2B as the lower part of the material) furthest removed from the actuated compressive device 215 retain their original structure. This can be employed to create an implant for biphasic tissues such as bone. The portion containing the collapsed pores 250 resembling cortical bone and the remaining portion remaining uncompressed 220 resembling cancellous bone.

Figure 2C:
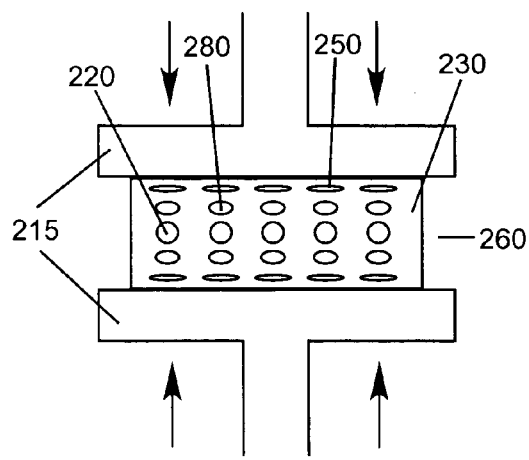
FIG. 2C shows the porous matrix material being compressed by both compressive devices.

As shown in FIG. 2C, dual gradient porous matrix materials 260 can be formed by compressing the porous matrix material with a plurality of actuated compressive devices 215, actuated either in succession or simultaneously. The compressed surfaces, containing the pores closest to the actuated compressive devices 215, will contain the highest proportion of sacrificed or compressed pores 250. The next layer contains the partially compressed pores 280 which have started to collapse, but initially will decrease in size before completely collapsing or being sacrificed. The porous matrix material furthest removed from the actuated compressive devices 215, in the middle of the dual gradient material 260, will have pores 220 that most closely maintain their original structure and size. This multiple compression technique depicted in FIG. 2C may be employed to create an implant for a triphasic tissue such as the skull, requiring an implant that mimics the transitions from cortical bone (more solid) to cancellous bone (porous) and back to cortical bone.

Figure 2D:
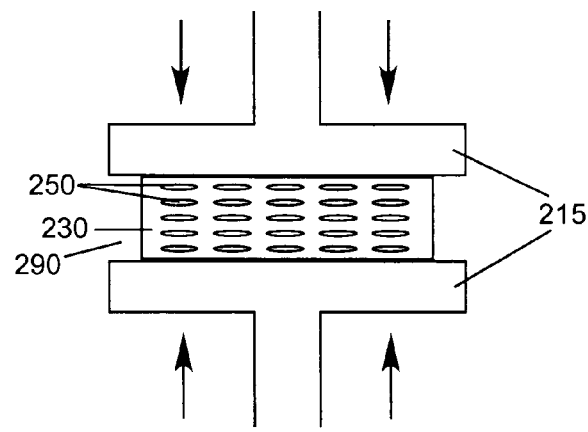
FIG. 2D shows the porous matrix material being compressed by both compressive devices in a heated atmosphere.

As shown in FIG. 2D, an evenly and significantly compressed porous matrix material may be created, such as by actuating the compressive devices 215 acting upon porous matrix material, by completely collapsing and sacrificing every pore. As a result, the evenly and significantly compressed material could be formed without any of the gradients created in devices of FIGS. 2B and 2C. As seen in FIG. 2D, the sacrificed or collapsed pores 250 can be distributed through out the material 290. This is useful in the creation of a superior implant to replace those currently manufactured from cortical bone, metal, or solid polymers.

An evenly compressed porous matrix material 290 may also be created by actuating the compressive devices 215 upon the material, while it is exposed to a heated atmosphere (e.g., convection oven, environmental control chamber, etc.). The heated environment may be above the glass transition temperature of the polymeric material. As a result, an evenly compressed material 290 could be formed without being significantly compressed and without any of the gradients created in the devices of FIGS. 2B and 2C. As seen in FIG. 2D, the sacrificed or collapsed pores 250 will be evenly distributed through the material 290.

It is envisioned that desired percentages of porosity or desired pore shapes and sizes can be created based on the amount and method of compression. Specific pore shapes (e.g., spherical, thin flat sheet, tubular, etc.) or sizes may promote different types of tissue ingrowth (e.g. bone or vascular tissue ingrowth). Based on desired porosity or pore structure, the porous matrix material may act as a cellular scaffold for various uses in tissue engineering.

In another embodiment, surfaces of the porous matrix material (whether partially compressed 240 depicted in FIG. 2B, a dual gradient material 260 in FIG. 2C, or evenly compressed 290 as shown in FIG. 2D) while in contact with actuated compressive devices 215, which may or may not be heated, could have compressed pores 250 forming extremely thin sheets. The extremely thin compressed pores 250 may form laminate walls, thus providing a confining matrix for confining new tissue growth within the device. This can be important for applications involving areas such as the spine where vital neural and vascular tissues are exposed and vulnerable.

In another embodiment, as illustrated in FIG. 3A, an uncompressed shape, (e.g., a sphere) 300 of porous matrix material is to be subjected to compressive forces in three dimensions, with the compressive forces to be applied depicted by arrows 310. This three dimensional compression may be applied in a variety of forms, for example mechanical means of compression, or alternatively by exposing the sphere 300 to a high pressure environment (e.g., increased atmospheric or hydrodynamic pressure). Pores 320 within a polymeric material 330 create the uncompressed sphere's 300 structure. As depicted in FIG. 3B, after application of compressive forces, the porosity and size of the compressed sphere 340 have been decreased. Unlike two-dimensional compression, the pores 350 have not collapsed into thin, laminate walls. The three-dimensional compression resulted in compressed pores 350, by reducing the pores in size, rather than inducing collapse. This decrease in the size of the sphere may be caused by folding of the pores resulting in a decrease in the constrained area within each pore, or an increase in wall thickness between the pores of the polymeric material (not shown). This embodiment may be implanted within the body for various purposes, for example as a device to promote staged delivery of biologically active agents or alternatively, the device or a section of the device may be used to create an implant in order to repair, replace or supplement a body part (e.g., a chin or a cheek). The embodiment of a three dimensionally compressed shape may also be used to create a cell based implant wherein the cells supported in the non-compressed center of the device are protected from the body's immune system by the collapsed porous exterior. This would be particularly useful in supporting and protecting transplanted tissue (autograft or xenograft) such as islate cells capable of producing insulin. While immune cells would be prevented from entering the sphere 340 and destroying the islate cells, oxygen and nutrients would readily pass through the collapsed pores 350. In turn, waste product and insulin would pass out of the sphere.

Two-dimensional compression may also be applied upon a shape (e.g., a cylinder) as illustrated in FIGS. 4A and 4B. Like the sphere 300 of FIG. 3A, the uncompressed cylinder 400 of FIG. 4A is composed of pores 410 within a polymeric material 420. Two-dimensional compression may be applied to the cylinder 400 by applying force around the circumference of the cylinder 400 while restricting elongation of its height. This type of two-dimensional compression may result in the smaller diameter compressed cylinder 430 of FIG. 4B. The compressed cylinder 430 may feature pores 440 that have been forced to narrow under two-dimensional compression yet maintain their relative height. If the elongation of the compressed cylinder 430 is encouraged (e.g., by tension applied at one or both ends of the cylinder), the pores within may narrow and lengthen (not shown). Depending on the amount of compression applied, the pores 440 could form thin tubes running parallel to each other throughout the height of the cylinder 430. Devices like this would be useful in various medical applications (e.g., as orthopedic rods, nerve guides, etc.).

It is recognized that the pores 440 can be compressed by a drawing or lengthening action of the cylinder 400. As porous materials are brought above glass transition, they soften and contract. If contraction is prevented and a force in a new direction is applied, the now malleable material may stretch to the extent that the porosity can collapse and the void volume is lost. This will allow the porous material to be shaped by being compressed into, stretched into, or drawn over a mold. In this way, porous sheet material can be stretched into concave molds or over convex molds allowing the formation of unique cup or cavity shaped sheets. In essence, the porous sheet material at or above glass transition can be thermoformed by any method known to those skilled in the art, including, for example, male/female molding and vacuum drawing. The area of the porous polymer that has been shaped is stiffer than the unaltered areas of the sheet. This is believed to be due to the forced alignment of the polymer partitions defining the pores.

The forced alignment of the pores can also be used to create a pseudo-elastic memory in non-elastic polymers. If a porous sheet is brought above glass transition and drawn in a single direction, the pores can collapse in the transverse direction while elongating in the longitudinal direction. After cooling below glass transition temperature, the sheet resists forces applied in the longitudinal direction, but will easily expand in the transverse direction by allowing the elongated collapsed pores to open up as the entire sheet shortens in the longitudinal direction. If the force in the transverse direction is released, the sheet springs back to its elongated form.

This process can also be applied to the compressed cylinder 430 in FIG. 4B. If the cylinder is compressed around its circumference with tension applied to both ends while being heated, the pores will be forced into alignment while being narrowed and lengthened. After cooling down, tension could be applied at various locations around the center of the cylinder. As the cylinder expands and bows in the middle, the central pores are widened, yet the top and bottom pores move closer to each other. When the tension is released, the cylinder and pores return to their normal compressed shape and size.

A device having elongated pores capable of widening movement in the transverse direction could be used a ligament or tendon. In a tubular form, it could be useful as a vessel, nerve guide, esophagus or other tubular organs. Additionally, it could be used as a sleeve, sack, or bag stretched over or around implants (e.g., rods, nails, etc.) or used to hold materials, for example granular materials such as ceramics (e.g., hydroyapatite, tricalcium phosphate, etc.), or other materials such as tissues (e.g., cells, bone chips, demineralized bone, bone marrow aspirate, etc.).

Figure 5:
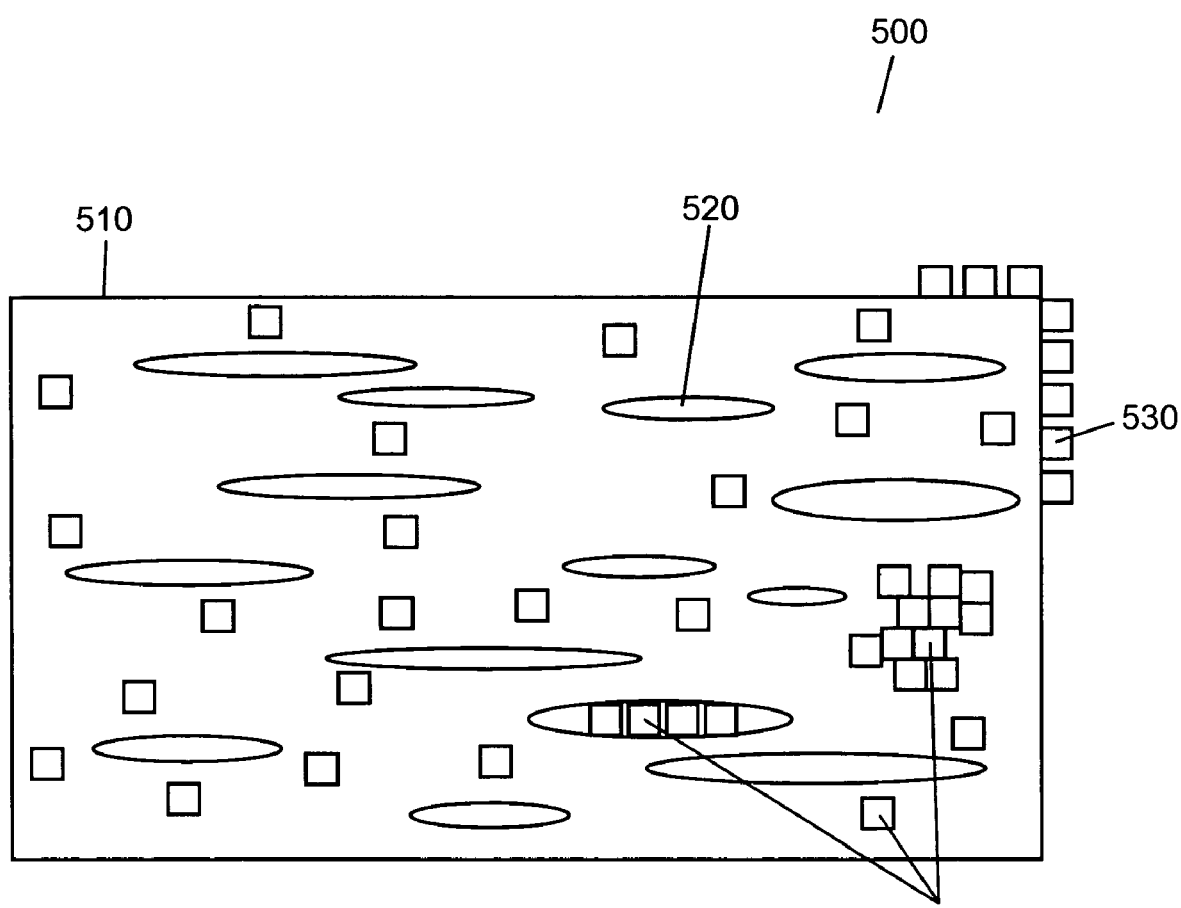
FIG. 5 shows the pore structure of compressed porous matrix material that contains various additive materials.

In another embodiment as illustrated in FIG. 5, a compressed polymer matrix material 500 may be created in a common shape (e.g., a block, a sphere, etc.) and/or shaped, machined, or molded to fit a particular application, with the material further containing or coated with at least one additive component 530. These additives may be associated with only the surface 510 of the polymer matrix material, rather than extending into the interior of the shaped material (e.g., serving as a coating or shell). Alternatively, the additives 530 may be distributed throughout and incorporated into the material 500 and/or the pores 520, either in a random or non-random dispersion. In an embodiment of the device having a random dispersion of the additives 530, the additives may be uniformly distributed throughout the volume of the polymer matrix material 500. In another embodiment, the additive 530 may be distributed non-randomly, i.e., having a non-uniform distribution of additive 530 within the polymer material 500, or within a depot within the material 500. The non-uniform distribution may impart a desired quality to the material (e.g., by selectively affecting a portion of the material 500, by providing the ability to deliver a drug or multiple biologically active agents as a burst and/or over an extended period of time, etc.). In another embodiment, the additives 530 may be associated with only the pores 520 within the polymer matrix material 500. In any of the embodiments containing additives, the pores may be open or closed cell, random or interconnected.

In one embodiment, at least one of the additives 530 of FIG. 5 may serve to reinforce the polymer matrix material 500. The reinforcing additives 530 serve to enhance the characteristics of the device, such as mechanical strength (e.g., modulus of elasticity, compressive strength, tensile strength, etc.) and biodurability (e.g., hydrolytic degradation, strength retention, etc.). This may be accomplished by incorporating reinforcing elements (e.g., mesh, fibers, threads, screen, etc.) onto the surface, or incorporated into the material 500 (e.g., uniformly dispersed or individual layers) and/or the pores 520 of the polymer material. To further improve the mechanical properties of the material, the reinforcing elements may be interwoven, layered, or compacted together during the manufacture of the uncompressed polymeric material, or as a result of compression in making the compressed polymeric material 500.

In another embodiment, at least one of the additives 530 of FIG. 5 may include or be a biologically active agent (e.g., growth factors, demineralized bone material, cells, drugs, viruses, etc.). The unique porous structure of the compressed material 500 can be used to control the location and delivery of the biologically active agents. The formation of the construct controls the flow of fluid (e.g., blood, interstitial, etc.) within the device allowing for tailored release properties. The biologically active agents may be incorporated into the device along with reinforcing agents, in which case, it is recognized the biologically active agents may be mechanically or chemically attached or bonded to the reinforcing materials. Alternatively, it is also recognized that any of the additives 530 (e.g., reinforcing or biologically active agents) may be delivered together in the material 500 of the device without being mechanically or biologically bonded. Examples of biologically active agents that may be delivered in the device are shown in following Table 2.

TABLE 2

Examples of Biological Active Ingredients

Adenovirus with or without genetic material
Alcohol
Amino Acids
    L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
    GP IIb-IIIa inhibitors
        eptifibatide
Anti-proliferation agents
    Rho Kinase Inhibitors
        (+)-trans-4-(1-aminoethyl)-1-(4-pyridylcarbamoyl)
        cyclohexane
Anti-rejection agents
    Rapamycin
Anti-restenosis agents
    Adenosine $A_{2A}$ receptor agonists
Antisense
Antispasm agents
    Lidocaine
    Nitroglycerin
    Nicarpidine
Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)

TABLE 2-continued

Examples of Biological Active Ingredients

MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
Cellular materials
    Adipose cells
    Blood cells
    Bone marrow
    Cells with altered receptors or binding sites
    Endothelial Cells
    Epithelial cells
    Fibroblasts
    Genetically altered cells
    Glycoproteins
    Growth factors
    Lipids
    Liposomes
    Macrophages
    Mesenchymal stem cells
    Progenitor cells
    Reticulocytes
    Skeletal muscle cells
    Smooth muscle cells
    Stem cells
    Vesicles
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Drugs
Etretinate
Genetic material
Glucosamine
Glycosaminoglycans
GP IIb/IIIa inhibitors
    L-703,081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)

TABLE 2-continued

Examples of Biological Active Ingredients

Platelet-derived endothelial cell growth factor (PD-ECGF)
Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
inflammatory mediator
Insulin
Interleukins
Interlukin-8 (IL-8)
Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins
Proteoglycans
    Perlecan
Radioactive materials
    Iodine—125
    Iodine—131
    Iridium—192
    Palladium 103
Radio-pharmaceuticals
Secondary Messengers
    Ceramide
Somatomedins
Statins
Stem Cells
Steroids
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The inclusion of groups and subgroups in the tables is exemplary and for convenience only. The grouping does not indicate a preferred use or limitation on use of any material therein. For example, in Table 2, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

In another embodiment, at least one of the additives 530 of FIG. 5 may be in the form of particulate components or filler materials (e.g., tricalcium phosphate, biphasic calcium phosphate, hydroxylapatite, calcium sulfate, tetracalcium phosphate, autologous bone graft, allograft bone matrix, polymers, microspheres, etc.), which enhance the functionality of the device. The particulate components may be delivered within the polymeric material 500 in various forms (e.g., granules, chips, powders, gels, etc.). The incorporation of particulate components into the polymeric material 500 may enhance the ability of the device to exhibit desirable biological qualities (e.g., cellular growth promotion, bioactive osteoconductivity, tissue ingrowth promotion, etc.). Furthermore, the particulate components may also serve to enhance the mechanical strength of the material. A non-exhaustive list of additive materials 530 that may be incorporated in the present invention in the form of particulate or filler materials is provided in Table 3.

TABLE 3

Examples of particulate or filler materials suitable
for use in the present invention Alginate
Bioglass
Calcium
Calcium Phosphate
    Monobasic
    Dibasic
    Tribasic
Ceramics
Chitosan
Cyanoacrylate
Collagen
Dacron
Demineralized bone
Elastin
Fibrin
Gelatin
Glass
Gold
Hyaluronic acid
Hydrogels
Hydroxy apatite
Hydroxyethyl methacrylate
Nitinol
Oxidized regenerated cellulose
Phosphate glasses
Polyethylene glycol
Polyester
Polysaccharides
Polyvinyl alcohol
Radiopacifiers
Salts
Silicone
Silk
Steel (e.g. Stainless Steel)
Synthetic polymers
Thrombin
Titanium In another embodiment, at least one of the additives 530 of FIG. 5 may serve to impart or create a microstructure within the macrostructure of the polymeric material 500. Preferably, the macrostructure may serve to maintain the mechanical, architectural, and structural stability of the device and provide a biologically inert surface for tissue ingrowth. The microstructure additive may, in a preferred embodiment, serve to attract and nourish inbound cellular growth. The additive material 530 suitable for creating a microstructure can be selectively varied within certain regions of the macrostructure to promote or deter different biologic characteristics critical to different tissue requirements. The microstructure creating additive 530 could be contained by or concentrated within the compressed pores 520. The microstructure can be strategically located within one or more compressed pores 520. The microstructure creating additive 530 may also be on the surface 510 of the macro structure. When located within collapsed intercommunicating pores, the microstructure may prevent complete collapse of the pore. The volume of microstructure can be used to control the percentage collapse of each pore. The space created by the microstructure, as well as the hydrophilic/hydrophobic properties of the microstructure, influence the rate at which fluids and/or cells flow into and out of the collapsed pores. In this way, microstructure could be used to control the release kinetics of other additive materials, such as biologically active agents, supported within the polymer or within the microstructure itself, from the device.

It is recognized that any of the above-described additive agents 530 may be used alone or in combination with other additive materials. It is also recognized that individual components making up the additive materials may serve a dual purpose as an additive (e.g., acting as a biologically active agent and a reinforcing agent concurrently). When more than one additive 530 is used within the polymer material 500, the additives may function separately, or have a synergistic effect, wherein the activity of one class of additive 530 helps the activity of the other class of additive component 530. The additives may physically be bonded together, or merely placed in proximity with each other, or even distributed randomly or non-randomly without any interrelationship. It is also recognized that based on the physical characteristics of the additive components, some of the components may not resorb or may resorb into the body at a different rate from other components, or have similar or different temporal qualities, such that the effects of the different additives may persist for various durations.

Figure 6A:
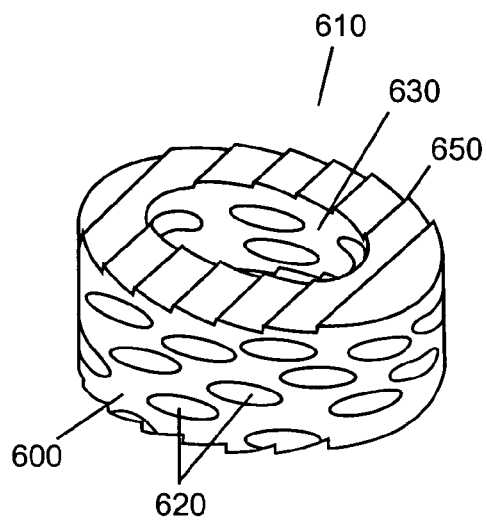
FIG. 6A is a perspective view of one embodiment of the implant.

In another embodiment, shown in FIG. 6A, a resorbable spinal implant in the form of an interbody fusion device (e.g., spinal cage, spacer, wedge, etc.) 610 may be created from the compressed porous matrix material 600. An interbody fusion device 610, once implanted using techniques known in the art, may serve to restore the disc space in a spinal column. An interbody fusion device created utilizing the material 600 of the present invention may be used to provide a large surface area to provide for adequate bone ingrowth, thereby eliminating the need for the prior art technique of bone harvesting for autografts to be used in creating a spinal implant.

The device of the present invention may also be constructed as a spinal implant for posterolateral fusion (not shown). A posterolateral spinal implant spans and contacts the transverse processes of adjacent vertebrae. The posterolateral implant made in accordance with the present invention will maintain a space above and across the transverse processes and facilitate new bone formation.

The device of the present invention may be constructed as an anterior fusion spinal implant (not shown). An anterior spinal implant would fasten to two vertebrae and span the operative disc space, thereby serving to restrict motion and promote fusion through bone growth.

In an embodiment of the present invention, the compressed pores 620 within spinal implant device 610 may be of any size or shape and arranged in any orientation suitable for use as a spinal implant. Preferably, the compressed pores 620 would be formed as thin, laminate sheets, which enable the device 610 to withstand both large compressive loads and cyclic loading. In a more preferred embodiment, the structure and design of the device 610 will give it desirable mechanical properties (e.g., compressive strength, modulus of elasticity, tensile strength, etc.) similar to cortical and/or cancellous bone.

In another embodiment, one or more channels 630 (e.g., pores, holes, slots, perforations, etc.) may be molded, machined, or drilled into the material of the present invention, for example as shown in FIG. 6A depicting a spinal implant. Channels 630 can be created in any orientation or direction into or through the device 610. Channels 630 may pass completely through the device 610 thereby forming at least one void or reservoir from top to bottom or from side to side, at any angle. The size of the channels 630 can vary or may be the same. It is recognized the compressed pores 620 and channels 630 may provide a structural function and/or biological function. In the example of a spinal implant, the channels 630 may provide a scaffold for vascularization and/or bone ingrowth, in order to facilitate the occurrence of spinal fusion. The channels 630 may also serve to facilitate resorption of the polymer from which the device has been made by reducing the bulk or amount of polymer per device. Additionally, less polymer per device may lead to decreased manufacturing costs, as raw material consumption is reduced. For example, for similar sized objects, one solid polymer and another being 10% porous material prepared as described herein, the porous material utilized 10% less raw material, and may possess markedly better physical characteristics.

Figure 6B:
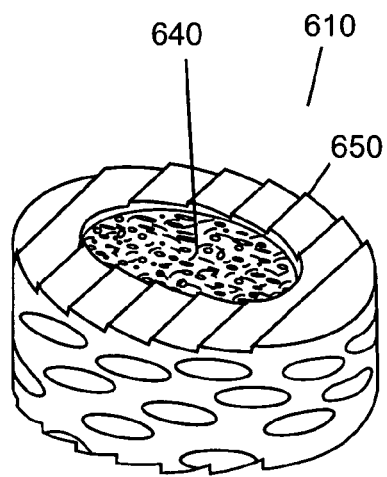
FIG. 6B is a perspective view of one embodiment of the implant containing an osteogenic material.

With reference to FIG. 6B, a channel (e.g., osteoconductive pore) or channels created in the material of the present invention may also be useful for the introduction of various biodegradable materials or matrices 640. For example, material constructed as a spinal fusion implant device 610 may feature a channel or hole (as depicted by channel 630 of FIG. 6A) that has been filled with material 640. In a preferred embodiment, one material 640 that may be contained in the channel(s) is osteogenic grafting material (e.g., bone grafts, demineralized bone, bone void fillers, hydroxypatite, bone chips, bioceramics, etc.) to promote bone ingrowth into and through the device 610. The channel 630 may be packed with the osteogenic material, which may be provided in various forms (e.g., chips, strips, sheets, sponges, gels, etc. Potential biodegradable matrices 640, which may at least partially fill the channel (s), may include beneficial materials (e.g., collagen sponge, collagen-ceramic composites, open-cell polylactic acid (OPLA), etc.) The materials or matrices may act as carriers for bone growth factors or osteogenic proteins, such as naturally or genetically engineered bone morphogenic proteins (i.e., BMP-2, BMP-4, etc.).

Referring again to FIG. 6A, in one embodiment of the device a channel 630 may also be used to accommodate a suitable tool (not shown) to facilitate insertion of device 610 into the living being. For example, in the case of a spinal implant, a tool may be inserted into the channel 630, thereby allowing controlled placement of the spinal implant into a vertebral disc space. The channel 630 and corresponding tool may or may not be threaded, or provide some temporary locking arrangement (e.g., keyed, friction fit, etc.) to provide extra control during implantation, wherein movement of the tool relative to the channel 630 may be limited.

In various embodiments, the compressed porous matrix material 600 can be conveniently machined or molded during compression to form spinal implants with complex geometries and various features. For example, polymer spinal implants may be created in a variety of different configurations (e.g., a horizontal threaded cylinder, a vertical ring, an open box cage, etc.). A gripping means 650 may be provided to ensure adequate stability of the implanted spinal device 610. The gripping means may be any features that prevent the device from sliding or undesirable shifting from the implantation site. These gripping means 650 may operate as a friction fit or incorporate locking elements (e.g., teeth, serrations, ridges, grooves, threads, wedges, blocks, pins, nails, screws, staples, etc.), which may be machined or molded into the device 610. For the example of a spinal fusion implant, the gripping means 650 have the ability to grasp the vertebral endplates and resist lateral movement, thus helping to prevent the implant from migrating out of the vertebral disc space. Additionally, the gripping means 650 may serve to impart increased surface area to the implant device 610, in order to allow the device to withstand spinal pressures. Any recesses created in the gripping means 650 (e.g., the spacing between consecutive teeth or threads) may also serve to facilitate bone ingrowth that may aid in anchoring the device in place. In an embodiment relying on threads functioning as the gripping means 650, the threads may be machined or molded on the outer surfaces of a compressed porous matrix shaped material (e.g., a dowel) to form a device similar to a threaded screw. The threads allow easy and controlled insertion into the vertebral disc space.

In another embodiment, a device 610 may be shaped like a rod (not shown). The rod may feature a gripping means (e.g., ridges or teeth). It is recognized that a device in the shape of a rod may beneficially incorporate a taper, such that one end is larger than the other, or alternatively, the rod may lack a taper.

Figure 6C:
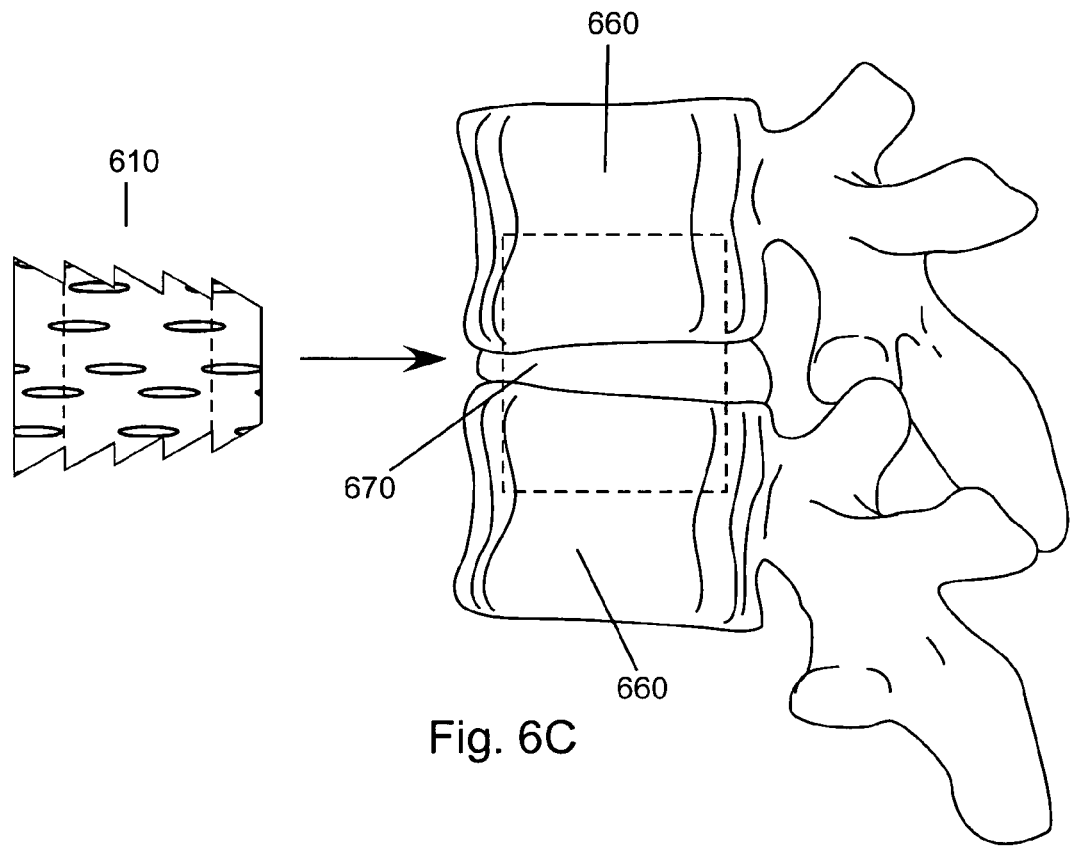
FIG. 6C is a perspective view of the embodiment from FIG. 6A and one of the anatomical locations that is suitable for treatment by the implant.

In another embodiment, as illustrated in FIG. 6A, a spinal cage 610 can be fabricated from the porous matrix material 600 into a spacer in the shape of a wedge. The wedge shaped device 610 may serve to provide vertebral spacing and may aid in interbody fusion between vertebrae. The cage or spacer device 610 may be tapered to provide the correct orientation to the vertebrae with which the device is in contact and can also serve to keep the device in place. It is recognized the spacer may be machined into any other shape or size (e.g., cylindrical, as shown in FIG. 6A, rectangular, kidney shaped, etc.) in order to conform to the shape of the vertebral endplates. Gripping means 650 may be machined into the cage 610 for additional spinal stability. The gripping means 650 may be any height, shape, or size, depending upon the intended use of the device 610. The gripping means 650 may be located on one or more surfaces of the device 610 and oriented in one or more directions on the device 610. As shown in FIG. 6C, the device 610 is sized and configured for engagement between two vertebrae 660. Preferably, the implant device 610 has a height approximately equal to or slightly greater than the height of the intervertebral disc space 670.

In various embodiments, the porous matrix material may be composed of layers of the same or different types of polymers. Two or more different porous polymer may be included in one device. It is recognized that this invention may be useful for medical devices that require specific abilities, material or mechanical properties, or biological conditions to function optimally in the body. For example, devices may undergo changes in loading over time, require specific degradation rates, may be loaded differently across the surface of the implant, etc. In order to accommodate the special requirements of some devices, in an embodiment, two or more different compressed porous matrix materials may be layered (e.g., stacked on one another, or alternatively side-by-side) to form the device. Alternatively, the same porous matrix material may be compressed under different conditions. In these layered embodiments, the layers of compressed material or materials may possess variable material and structural characteristics (e.g., degradation rates, flexibility, drug delivery rates, etc.). The layers may or may not be fused together. The layers may be compressed by different methods or by different amounts. The layers may provide the device the ability to be multi-functional. For example, it is recognized that one or more layers can perform one function (e.g. provide structurally integrity, maintain shape, etc.) for the device while one or more other layers perform another function (e.g., drug delivery, allow bone ingrowth, etc.).

In another embodiment, the compressed porous matrix material can be machined or molded into any configuration, such as an internal fixation device for use in surgical repair, replacement, or reconstruction of damaged bone in any area of the body. Internal fixation devices may be successfully employed for many conditions and applications (e.g., orthopedic, spinal, maxiofacial, craniofacial, etc.).

Figure 7:
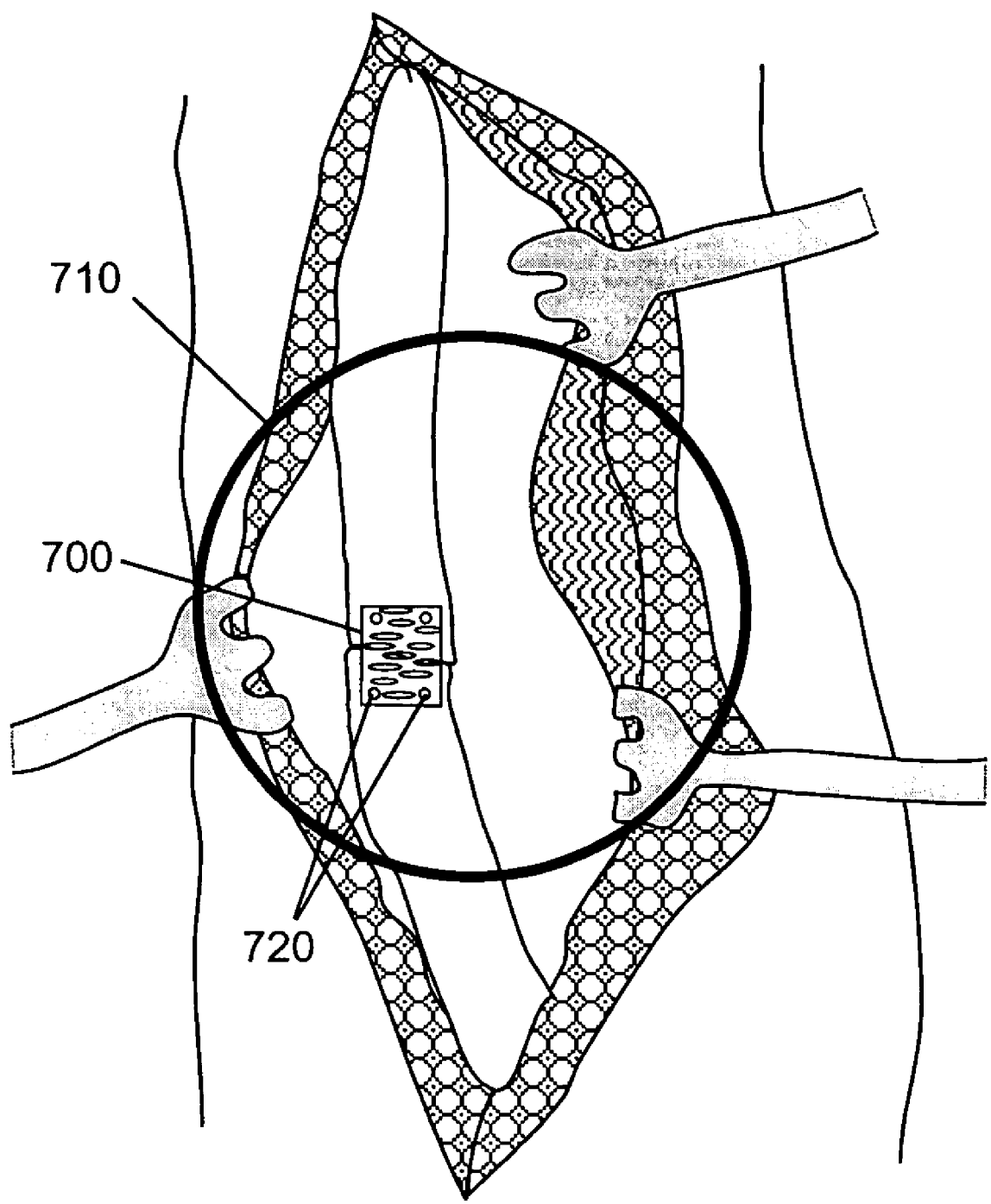
FIG. 7 is a perspective view of an alternative embodiment of the implant and one of the anatomical locations that is suitable for treatment by the implant.

Another possible embodiment of the invention is an internal fixation device, as shown in FIG. 7, where a plate 700, is affixed in an anatomical location 710. A plate 700 may be machined or molded with fixation holes 720 that will allow fixation to bone by various means known in the art (e.g., staples, screws, tacks, etc.). During the surgical implantation procedure, the fixation holes 720 may also be created to fit the anatomical location 710. Holes 720 created contemporaneously with implantation of the plate may allow more accurate placement or fitting of the plate 700, consequently a more effective application of the invention. The plate may be useful as a graft containment device for the repair or reconstruction of defects, such as those caused by surgery, tumors, trauma, implant revisions, infections, and also for joint fusion.

Figures 8A, 8B:
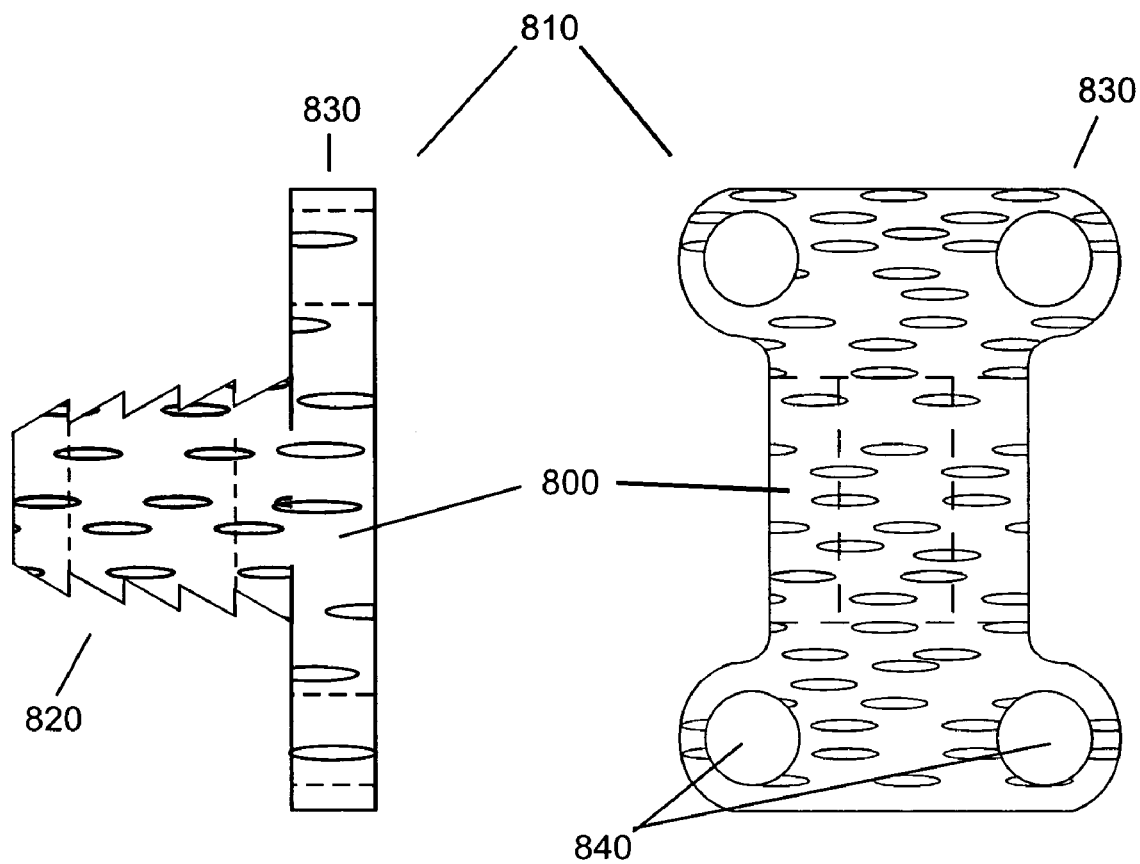
FIG. 8A is a perspective side view of an alternative embodiment of the implant.
FIG. 8B is a perspective front view of the embodiment from FIG. 8A.

In another embodiment, illustrated in FIGS. 8A and 8B, compressed porous matrix material may be machined or molded into an interbody fusion plating system 810, which is a device that is a combination of a cage or spacer 820 and a plate 830. The interbody fusion plating system 810 provides the benefits of a resorbable cage or spacer 820, and further incorporates the advantages of a plate 830. The plate 830 may increase fusion rates by acting as an anterior tension band, reducing motion and movement at the implantation level. The plate 830 will prevent the migration and loosening of the cage 820. The resorption of the plate 830 over time will gradually increase loading on the cage 820 and bony tissue, promoting fusion. The interbody fusion plating system 810 may be fabricated as one solid device or two single devices that can be connected and used together or used separately. The plate 830 may be machined with fixation holes 840 that will allow fixation to bone by means known to those skilled in the art (e.g., staples, screws, tacks, etc.). Alternatively, the fixation holes 840 may be created in the device contemporaneously with implantation, in order to ensure proper placement of the fixation holes in the device.

Figure 9A:
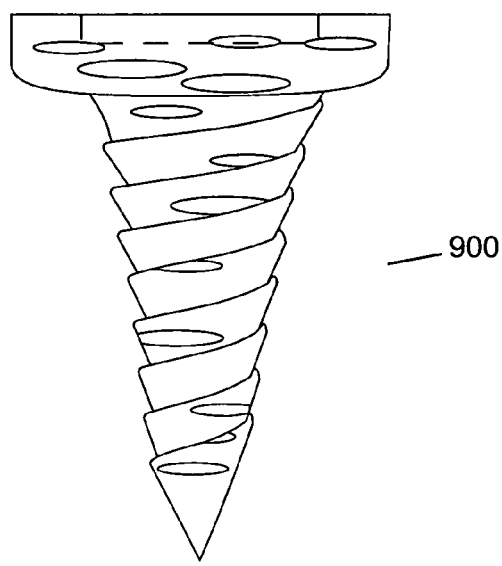
FIG. 9A is a perspective view of an alternative embodiment of the implant.
Figure 9B:
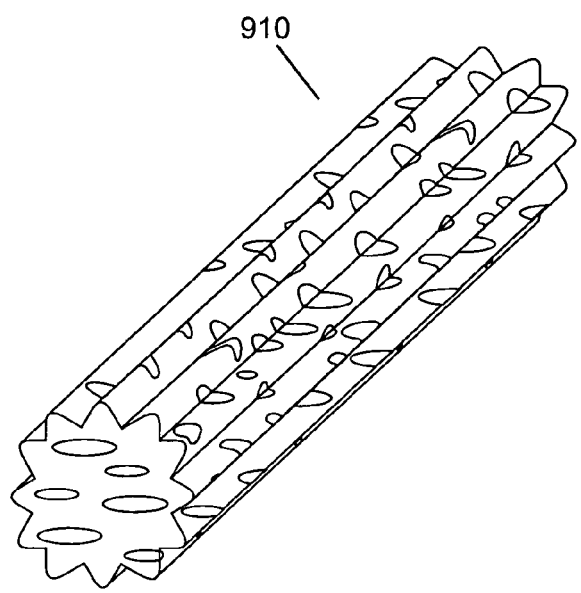
FIG. 9B is a perspective view of an alternative embodiment of the implant.
Figure 9C:
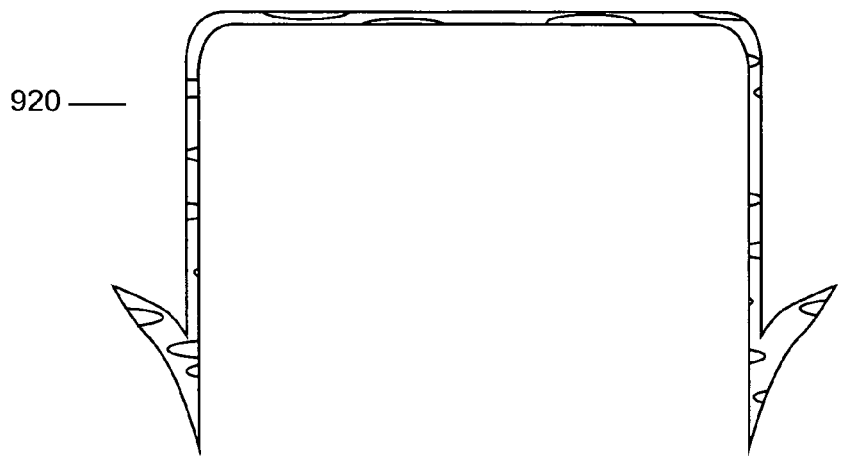
FIG. 9C is a perspective view of an alternative embodiment of the implant.

Various representative embodiments are illustrated in FIGS. 9A, 9B, and 9C, wherein medical devices may be fabricated into any configuration from the compressed porous matrix material. Such devices may be used in any field wherein the functionality of the porous polymer material as a fixation device may be useful, including but not limited to the fields of internal fixation, trauma repair, sports medicine, etc. For example, these devices suitable for bone and soft tissue fixation may include screws 900, rods, pins 910, tacks, arrows, staples 920, washers, nails, anchors, etc. These devices may be used in many applications requiring fixation devices, such as the repair of fractured bones.

The following examples are given for purposes of illustration to aid in understanding the invention and it is to be understood that the invention is not restricted to the particular conditions, proportion, and/or methods set forth therein.

Example 1

The objective of this example is to compare the physical properties of different Poly-1-lactide (PLA) porous matrix materials after being compressed 0, 40, 60, and 80% of its original height. Static axial compression tests were performed to measure the maximum compressive loads of the porous matrix materials after being compressed to different percentages of their original height. The compression tests will demonstrate the compressed material's mechanical properties can be altered and controlled over a wide range of possible values. The final properties of the compressed material are determined by the properties of the starting material and the amount of compression used. The final product is a material that has tensile and compressive strengths similar to that of non-porous polymer yet is not as stiff or subject to failure by cracking as non-porous polymer. The mechanical and porosity tests will assure a device fabricated from compressed porous matrix material (e.g., a spinal interbody fusion device) is able maintain its porosity and absorb fluids, while still being able to withstand large stresses and loads it may be subject to (e.g., the maximum physiologic loading expected in the lumbar spine of at least 10,000 N).

The compression test procedure for the compressed porous matrix materials are based on ASTM standards D1621-94, Standard Test Method for Compressive Properties of Rigid Cellular Plastics, and D1667-97, Standard Specification for Flexible Cellular Materials—Vinyl Chloride Polymers and Copolymers (Closed-Cell Foam). The only polymer used for this example was Poly-1-lactide (PLA). The porous matrix materials were produced by methods known to those skilled in the art. The porous matrix materials can be created with porosities that initially range from 98% to 86% or lower. At least five cylindrical specimens (15 mm in diameter and 15 mm in height) were machined from each material. An axial load was applied via a materials testing system to each cylindrical specimen at a rate of 12.5 mm/min until a stopping point of 50% strain. The load versus displacement curves were recorded. For each test, the maximum compressive load and compressive modulus of elasticity were calculated and recorded.

Additional material property tests included porosity and wettability. The wettability and porosity were measured to determine the effects of compression on the porous material. The porosity of each material was measured before and after being compressed using a Helium Pycnometer, which determines the density and volume of a sample by measuring the pressure change of helium in a calibrated volume. The wettability (ability of the material to absorb fluids) of the material was determined on a pass/fail basis after compression, subjectively assessing the ability of the porous material to absorb fluids.

The different PLA materials with initial porosities ranging from 97% to 86% were compressed by 0% to 84% of its original height. Up to the maximum compression of 84%, the materials maintained their wettability and a percentage of the original pre-compressed porosity. The material's strength after compression was directly related to the initial porosity and amount of compression. For example, the initial porosity and compression strength of the uncompressed materials ranged from 97% porosity with 30 N of compressive strength to 86% porosity with 624 N of compressive strength. At 40% compression, the strength and new porosity for the two materials with the lowest and highest initial porosities ranged from 67 N and 94% porosity (97% initial porosity) to 1348 N and 75% porosity (86% initial porosity). The compressive strength and porosity ranged from 101 N and 90% (97% initial porosity) to 2249 N and 71% porosity (86% initial porosity) after 60% compression. The final compression set point of 80% resulted in compressive strengths and porosities ranging from 326 N and 84% porosity (97% initial porosity) to 4889 N and 57% porosity (86% initial porosity).

In order to find a compressive strength greater than 10,000 N, the material with the lowest initial porosity (86%) was compressed by 84% of its original height. At the 84% compression, the maximum compressive load was 12,985 N and the actual measured porosity was 41%. Relying on the following equation, where theoretical porosity can be calculated as $1-[(1-\text{initial \% porosity})/(1-\% \text{ compression})]$, the theoretically calculated porosity would have been around 13%, with the difference between the theoretical and actual porosity percentage values most likely being due to the sample not being restrained as compression was applied, and allowed to expand horizontally beyond the 15 mm diameter of the original sample. Had there been some restraint against expansion while being compressed, the percentage porosity would have been reduced to less than 14% porosity, down from the original 86% of the initial material. The maximum compressive load of 12,985 N is above the maximum expected physiological spinal loading of 10,000 N. The porous matrix material can be produced with a lower initial porosity and compressed by various methods (previously described) to increase the maximum compressive strength, providing a significant safety factor compared to both typical and maximum physiological spinal loading.

The results from the porosity, wettability, and compression tests prove that PLA porous matrix material can be compressed by various degrees to give a wide range of compressive strengths while still maintaining its porosity. By altering PLA porous material and the amount of compression, any amount of porosity and compressive strength may be created. The compressive strengths were found to range from 30 to almost 13,000 N. The compressed material may be useful as an internal fixation device, such as a spinal fusion cage. A spinal fusion cage made of compressed porous matrix material would be able to withstand the maximum physiologic loading expected in the lumbar spine of at least 10,000 N. The maximum compressive load found in this example of 12,985 N is above the maximum physiological spinal loading. Even accounting for the horizontal expansion during compression, the increased area that results is less than the surface area of a lumbar vertebra and thus still exceeds the expected load. The porous matrix material can be produced with a lower initial porosity and compressed by various methods (previously described) to increase the maximum compressive load providing a significant safety factor compared to both typical and maximum physiological spinal loading.

Example 2

While Example 1 demonstrated that PLA porous matrix materials could be compressed, this example serves to illustrate that porous matrix materials made of different polymers can also be compressed and will compare the physical properties of the two compressed materials. Polylactide/Poly ε-Caprolactone (PLA/PCL) and Poly(desaminotyrosyl-tyrosine ethyl carbonate) (PDTE) Carbonate were used to create two different porous matrix materials. The compression, porosity, and wettability tests described in Example 1 were used to test these materials.

Static axial compression, wettability, and porosity tests were conducted as described in the EXAMPLE 1.

Before compression, the porosities of the PLA/PCL and PDTE Carbonate were 92% and 94%, respectively. Up to 40% compression, the materials show little to no change in porosity. At 80% compression, the more brittle porous material (PDTE Carbonate) had a porosity of 73% compared to 66% porosity for the PLA/PCL material. It should be noted that, as in EXAMPLE 1, the samples were not restrained from expanding horizontally during compression; therefore the actual measured porosity values are slightly different from theoretically calculated porosity values.

The maximum compressive strength results showed significant differences in the mechanical strength of the compressed materials. At 80% compression, the PDTE Carbonate had a maximum compressive strength greater than 1500 N compared to a compressive strength of 450 N for the PLA/PCL material. At 87% compression, the PLA/PCL with 59% porosity was able to withstand a maximum compressive load of 581 N.

The objectives of this study were to determine if different materials (other than PLA) could be compressed and to compare the material and mechanical properties of two different porous matrix materials (PLA/PCL and PDTE Carbonate) after being compressed different percentages of their original height. Due to the elasticity of the PLA/PCL material, it would only hold its shape if compressed at temperatures near its glass transition temperature. The PDTE Carbonate could be compressed with or without heat and hold its compressed shape. After compression, each material still retained a high percent of its porosity and was able to absorb fluids. The compressive strength results from the compressive tests were significantly different for each material. The PLA/PCL material had a compressive strength much less than the PDTE Carbonate material. The elasticity of the PLA/PCL material prevents it from being a material able to withstand large compressive loads. This study proves that it is possible to compress elastic and brittle materials, as well as non-lactide materials.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. A porous implantable device suitable for implantation in a living being, said implantable device comprising a high density porous polymer material having at least one property that is characteristic of at least one of cortical bone and cancellous bone of a human vertebrae, said at least one property being selected from the group consisting of compressive strength, modulus of elasticity, and tensile strength, wherein said high density is obtained by a process comprising compression applied to at least one porous polymer material, wherein said compression process causes the sacrifice of at least some pores in said porous polymer material, thereby forming a new shape, and further wherein said compression takes place in at least one of (i) a temperature above the glass transition temperature for said polymer, and (ii) when said polymer is in a plasticized condition, whereby molecules of said polymer move and rotate to achieve a lower energy state, thereby causing said high density porous material to permanently lock in the new shape, and wherein said device is arranged for implantation into said living being.

2. The porous implantable device of claim 1, wherein said at least one polymer material is resorbable.

3. The porous implantable device of claim 1, wherein said pores are sacrificed to create laminar walls.

4. The porous implantable device of claim 1, wherein said high density porous material is further machined to a final shape.

5. The porous implantable device of claim 1, further comprising at least one additive component.

6. The porous implantable device of claim 5, wherein said additive component is distributed uniformly throughout the implantable device.

7. The porous implantable device of claim 5, wherein said additive component is distributed on outside surfaces of the implantable device.

8. The porous implantable device of claim 5, wherein said additive component is distributed within said pores of said implantable device.

9. The porous implantable device of claim 5, wherein said additive component is distributed in a portion of said implantable device.

10. The porous implantable device of claim 5, wherein said additive component is arranged to create a microstructure.

11. The porous implantable device of claim 10, wherein said microstructure is arranged to encourage tissue ingrowth.

12. A high density porous material comprising at least some sacrificed pores, suitable for implantation into a living being, having at least one mechanical property being at least characteristic of at least one of cortical bone and cancellous bone of a human vertebrae, and being obtained by the process comprising the steps of:
   a) providing at least one high porosity material comprising a plurality of pores in the form of cells, wherein said pores are defined by pore walls;
   b) inducing a glass-transition state within said at least one high porosity material;
   c) applying a compressive force within one or more dimensions while said high porosity material is in said glass transition state, said compressive force being sufficient to cause said molecules of said high porosity material to move and rotate to achieve a lower energy state, thereby causing said high porosity material to achieve a new size or shape, and further to sacrifice at least a portion of said pores, thereby creating said high density porous material; and
   d) cooling said high density porous material out of said glass transition state, wherein said high density porous material permanently maintains the new shape or size.

13. The high density porous implantable material of claim 12, wherein said high porosity material further comprises at least one polymer material.

14. The high density porous implantable material of claim 13, wherein said at least one polymer material is resorbable.

15. The high density porous implantable material of claim 12, wherein said process further comprises the step of:
   e) machining said high density porous material to a shape.

16. The high density porous implantable material of claim 12, wherein said high porosity material further comprises at least one additive component.

17. The high density porous implantable material of claim 16, wherein said additive component is distributed uniformly throughout said high porosity material.

18. The high density porous implantable material of claim 16, wherein said additive component is distributed on outside surfaces of said high porosity material.

19. The high density porous implantable material of claim 16, wherein said additive component is distributed within said pores of said high porosity material.

20. The high density porous implantable material of claim 16, wherein said additive component is distributed in a portion of said high porosity material.

21. The high density porous implantable material of claim 16, wherein said additive component is arranged to create a microstructure.

22. The high density porous implantable material of claim 21, wherein said microstructure is arranged to encourage tissue ingrowth.

23. The porous implantable device of claim 12, wherein said at least one mechanical property is selected from the group consisting of compressive strength, modulus of elasticity, and tensile strength.

24. A porous implantable device comprising a porous polymer that is compressed by at least about 40 percent and no more than about 87 percent of its original height, is arranged to maintain its compressed shape, and has at least one mechanical property being at least characteristic of bone of a human vertebrae.

25. The porous implantable device of claim 24, wherein said at least one mechanical property is selected from the group consisting of compressive strength, modulus of elasticity, and tensile strength.

26. The porous implantable device of claim 24, wherein said bone comprises at least one of cortical bone and cancellous bone.

* * * * *